(12) United States Patent
Xu et al.

(10) Patent No.: US 8,592,625 B2
(45) Date of Patent: Nov. 26, 2013

(54) PROCESS FOR RESOLVING S-3-(AMINOMETHYL)-5-METHYLHEXANOIC ACID

(75) Inventors: Jiankang Xu, Taizhous City Zhejiang (CN); Da Zhang, Taizhous City Zhejiang (CN); Meiqi Ye, Taizhous City Zhejiang (CN); Jie Chen, Taizhous City Zhejiang (CN); Yongbing Guo, Taizhous City Zhejiang (CN); Yongjiang Hu, Taizhous City Zhejiang (CN)

(73) Assignee: Zheinjiang Jiuzhou Pharmaceutical Co., Ltd., Taizhou, Zhejiang (CN)

( * ) Notice: Subject to any disclaimer, the term of this patent is extended or adjusted under 35 U.S.C. 154(b) by 633 days.

(21) Appl. No.: 12/811,418

(22) PCT Filed: Jan. 2, 2008

(86) PCT No.: PCT/CN2008/000012
§ 371 (c)(1),
(2), (4) Date: Jan. 3, 2011

(87) PCT Pub. No.: WO2009/082861
PCT Pub. Date: Jul. 9, 2009

(65) Prior Publication Data
US 2011/0098502 A1    Apr. 28, 2011

(51) Int. Cl.
*C07C 227/36*    (2006.01)
(52) U.S. Cl.
USPC ........................................ 562/401

(58) Field of Classification Search
USPC ........................................ 562/401
See application file for complete search history.

(56) References Cited

U.S. PATENT DOCUMENTS 5,637,767 A * 6/1997 Grote et al. .................. 562/553
2006/0270871 A1  11/2006 Khanduri et al.

FOREIGN PATENT DOCUMENTS

CN       1786703 A       6/2006

* cited by examiner

*Primary Examiner* — Yong Chu
(74) *Attorney, Agent, or Firm* — Blue Filament Law PLLC; Avery N. Goldstein

(57) ABSTRACT

The present invention relates to a process for resolving S-3-(Aminomethyl)-5-methylhexanoic acid, which adopts benzoyl-L-glutamic acid, 4-methyl benzoyl-L-glutamic acid, benzene sulfonyl-L-glutamic acid or 4-methyl benzene sulfonyl-L-glutamic acid as a resolution agent to make a first resolution to racemic 3-aminomethyl-5-methylhexanoic acid, and adopts the resolution agent same to that of the first resolution to make a second resolution to the first resolution product to obtain the second resolution product, thus the resolution salt product is obtained, and further hydrolyzed by an acid, the resolution agent is extracted to be separated, the pH is adjusted to be neutral, the product S-3-(Aminomethyl)-5-methylhexanoic acid, i.e. the pregabalin, is then precipitated by distillation, therefore the present invention has the characteristics of polluting the environment slightly, high efficiency and stability, simpleness and practicality, producing product with high purity and a low production cost, and is suitable for large-scale production.

11 Claims, No Drawings

PROCESS FOR RESOLVING S-3-(AMINOMETHYL)-5-METHYLHEXANOIC ACID

CROSS-REFERENCE TO RELATED APPLICATIONS

This application is the U.S. national phase of PCT/CN2008/000012 filed Jan. 2, 2008.

FIELD OF THE INVENTION

The present invention relates to the technical field of compound preparation, in particular to the technical field of the process for resolving S-3-(Aminomethyl)-5-methylhexanoic acid, more particularly to a process for resolving S-3-(Aminomethyl)-5-methylhexanoic acid.

BACKGROUND OF THE INVENTION

S-3-Aminomethyl-5-methylhexanoic acid, i.e. the pregabalin (PGB, the trade name Lyrica), the chemical name of which is (3S)-3-aminomethyl-5-methylhexanoic acid, the molecular formula of which is $C_8H_{17}NO_2$, the molecular weight of which is 159.23, is a white crystalline powder, and has a melting point of 184° C.-186'C. The pregabalin is a novel-type γ-aminobutyric acid (GABA) receptor agonist, can block voltage-dependent calcium channels and reduce the release of neurotransmitters, and is used in clinical for the treatment of the peripheral neuropathic pain, the pain caused by the diabetic peripheral neuropathy (DPN), the postherpetic neuralgia (PHN), and the ancillary treatment of part of the epileptic seizures.

The structural formula of the pregabalin is shown as follows:

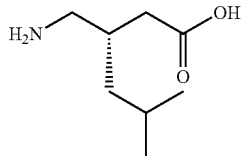

Pregabalin is an analogue of the neurotransmitter GABA, has the fat-solubility, and can pass through the blood-brain barrier. The mechanism is to reduce the calcium influx by inhibiting a subunit, the a2-σ protein, of the voltage-dependent calcium channel of the central nervous system, so as to reduce the release of the excitatory neurotransmitter substances such as glutamate, norepinephrine, P substance and so on. For the racemic compounds of 3-aminomethyl-5-methylhexanoic acid, in the aspect of binding to these sites, the activity of the isomer (R) is only ¹/₁₀ of that of the isomer (S).

The U.S. Pat. No. 5,637,767 disclosed a method of preparing S-3-Aminomethyl-5-methyl hexanoic acid, and the specific process is described as follows: the racemic 3-aminomethyl-5-methylhexanoic acid and the S-mandelic acid are dissolved in a 97% (v/v) isopropyl alcohol aqueous solution and maintained at that temperature for a period of time, cooled and seeded to crystallize, then filtered to obtain the first resolution wet product of S-3-Aminomethyl-5-methylhexanoic acid-5-mandelic acid salt, after pumped dry, the wet product is added again into a 97% (v/v) isopropyl alcohol aqueous solution, to make the second resolution by adding a certain amount of S-mandelic acid, to obtain the resolution product of S-3-Aminomethyl-5-methylhexanoic acid-S-mandelic acid salt, after dried, the resolution product is heated to reflux in the 95% (v/v) THF aqueous solution and maintained at that temperature for a period of time, then cooled and filtered to obtain the crude product of S-3-Aminomethyl-5-methylhexanoic acid, after pumped dry, the crude product is refined directly in a 75% (v/v) isopropyl alcohol aqueous solution to obtain the fine product of S-3-Aminomethyl-5-methylhexanoic acid, i.e. the fine product of the pregabalin, and the total yield is about 25%.

The above-mentioned resolution process adopts the isopropyl alcohol as the solvent, and the S-mandelic acid as the resolution agent, for the S-mandelic acid is expensive, the cost is high, it further adopts the THF aqueous solution to hydrolyze, thus it is difficult to recover, and the pollution is serious, moreover the overall yield is low, and the purity is not high.

SUMMARY OF THE INVENTION

Aspects of the present invention generally pertain to a process for resolving S-3-(Aminomethyl)-5-methylhexanoic acid, which is highly-efficient, environmental-friendly, of a low cost, suitable for mass production, and can obtain S-3-Aminomethyl-5-methylhexanoate acid with high purity.

In order to realize the above aims, in a first aspect of the present invention, a process for resolving S-3-(Aminomethyl)-5-methylhexanoic acid is provided and comprises the following steps:
  a. Resolving racemic 3-aminomethyl-5-methylhexanoic acid as a raw material in a polar solvent by using benzoyl-L-glutamic acid, or 4-methyl-benzoyl-L-glutamic acid, or benzene sulfonyl-L-glutamic acid, or 4-methyl benzene sulfonyl-L-glutamic acid as a resolution agent, so as to obtain a resolution salt product;
  b. Hydrolyzing the resolution salt product by adding an acid, separating the resolution agent by extraction, adjusting pH to be neutral, then precipitating the product S-3-(Aminomethyl)-5-methylhexanoic acid by distillation.

In a further aspect, the resolution agent is benzoyl-L-glutamic acid or benzene sulfonyl-L-glutamic acid, the polar solvent is an aqueous solution or an alcohol aqueous solution; the resolving includes heating to dissolve the resolution agent and the raw material in the polar solvent, and maintaining that temperature for a period of time, then cooling, stirring and filtering the polar solvent to crystallize solids, washing and pumping the solids dry to obtain a first resolution product; the acid is hydrochloric acid, the separating the resolution agent by extraction adopts ethyl acetate, the pH is 7 and the temperature of the distillation is 70° C.~80° C.

In yet another aspect, the resolution agent is benzoyl-L-glutamic acid; the solvent is water; the mole ratio of the resolution agent to the raw material is 0.5~1.5:1, the period of time is 10 minutes~60 minutes, the temperature of stirring is 10° C.~80° C., and the time of stirring is 1 hour~20 hours.

In yet another aspect, the mole ratio of the resolution agent to the raw material is 1.1:1, the period of time is 15 minutes, the temperature of stirring is 20° C.~30° C., and the time of stirring is 4 hours.

In a further aspect, the alcohol aqueous solution is a methanol aqueous solution, an ethanol aqueous solution or an isopropyl alcohol aqueous solution, and the volume ratio of water to alcohol in the alcohol aqueous solution is 10:1~10:5.

In a further aspect, the resolving further includes making a second resolution to the first resolution product.

In yet another aspect, the second resolution includes heating to dissolve the resolution agent and the first resolution product in the polar solvent, and maintaining that temperature for a period of time, then cooling, stirring and filtering the polar solvent to crystallize solids, washing and pumping the solids dry to obtain a second resolution product In yet another aspect, the resolution agent of the second resolution is same to that of the first resolution, and the molar ratio of the resolution agent of the second resolution to the first resolution product is 0~1:1.

In yet another aspect, the molar ratio of the resolution agent of the second resolution to the first resolution product is 0.4:1.

In a further aspect, after the step a and before the step b, the process further comprises the step:

a1. Refining the resolution salt product by crystallization.

In a further aspect, after the step b, the process further comprises the step:

b1. Heating to dissolve the product S-3-(Aminomethyl)-5-methylhexanoic acid in a 50% (v/v) isopropyl alcohol aqueous solution, decolorizing the solution with activated carbon and filtering the solution, then refining the product by crystallization.

The beneficial effects of the present invention are as follows:

1. The solvent used in the present invention during the resolution is water, so there is substantially no pollution, during the hydrolysis, the product S-3-(Aminomethyl)-5-methylhexanoic acid can be precipitated in water only after the resolution salt product is hydrolyzed with an acid, the resolution agent is extracted with ethyl acetate, and the pH is adjusted to be neutral, moreover ethyl acetate can be recycled and reused, so as to pollute the environment slightly.

2. Since the solvent used in the present invention during the resolution is water, and the resolution agent can be prepared by oneself, the cost is relatively low, less than ⅙ of that of the S-mandelic acid, moreover ethyl acetate and isopropyl alcohol are only used respectively during the refinement after the hydrolysis, but these solvents can be recycled and reused, therefore the cost of the solvents is relatively low, and the cost of the raw material for producing per kg pregabalin is estimated to be able to reduce 1000~2000 RMB.

3. When the present invention adopts benzoyl-L-glutamic acid as the resolution agent, the total yield is 10% higher than that of the prior art, when the present invention adopts benzene sulfonyl-L-glutamic acid or 4-methyl benzene sulfonyl-L-glutamic acid as the resolution agent, the total yield is also similar to that of the prior art, moreover the chiral purity of the obtained S-3-(Aminomethyl)-5-methylhexanoic acid can reach 100%, thus the production efficiency is high, the purity of the obtained product is good.

PARTICULAR EMBODIMENTS OF THE INVENTION

The present invention adopts benzoyl-L-glutamic acid, 4-methyl benzoyl-L-glutamic acid, benzene sulfonyl-L-glutamic acid or 4-methyl benzene sulfonyl-L-glutamic acid as a resolution agent (the above-mentioned agents are prepared by reacting glutamic acid with benzoyl chloride, 4-methyl benzoyl chloride, benzene sulfonyl chloride and 4-methyl benzene sulfonyl chloride in an alkaline condition respectively) to make a first resolution to racemic 3-aminomethyl-5-methylhexanoic acid, and adopts one of the above-mentioned resolution agents to make a second resolution to the first resolution product to obtain the second resolution product, thus the resolution salt product is obtained, and further hydrolyzed by an acid, the resolution agent is extracted to be separated, the pH is adjusted to be neutral, the product S-3-(Aminomethyl)-5-methylhexanoic acid, i.e. the pregabalin, is then precipitated by distillation, and the process of the resolution reaction is shown as follows:

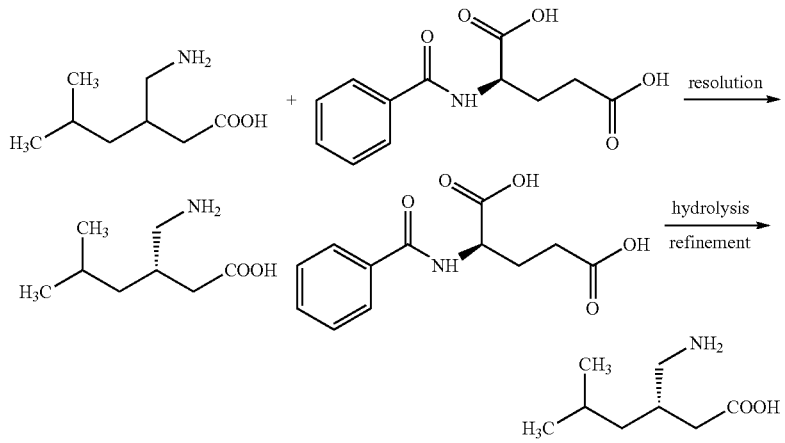

In order to understand the technical content of the present invention clearly, the present invention is further exemplified by reference to the following examples.

Example 1

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 34.5 g benzoyl-L-glutamic acid (Zhejiang Jiuzhou Pharmaceutical Co., Ltd., made by itself) and 200 ml water were added, then stirred and dissolved by heating, and maintained at that temperature for 15 minutes, cooled naturally to precipitate solids, then stirred at 20~30° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6 g benzoyl-L-glutamic acid and 150 ml water were added, then stirred and dissolved by heating, and maintained at that temperature for 15 minutes, cooled naturally to precipitate solids, then stirred at 20~30° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product and 100 ml water were added, then stirred and dissolved by heating, and maintained at that temperature for 15 minutes, cooled naturally to precipitate solids, then stirred at 20~30° C. for 2 hours, and filtered, the solids obtained were rinsed with the mother solution first and then a small amount of water, and pumped dry, thus 21.8 g refined resolution salt product was obtained. Yield ratio: 42.3%.

4. Hydrolysis

In a clean 250 ml 4-mouth flask, 21.8 g refined resolution salt product and 100 ml water were added, then stirred and 9 ml refined hydrochloric acid was added, after the product was dissolved, the solution was maintained at that temperature for 30 minutes, the resolution agent was extracted with (50+25+25) ml ethyl acetate, then the pH was adjusted to about 7 by adding about 25 ml 20% sodium hydroxide solution, the solution then was distilled under reduced pressure at 70~80° C. to about 40 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 7.6 g crude hydrolyte was obtained. Yield ratio: 90%.

5. Refinement

In a clean 250 ml 4-mouth flask, 7.6 g crude hydrolyte, 38 ml water and 38 ml isopropyl alcohol were added, then stirred and dissolved by heating, after dissolved completely, decolorized by adding 0.5 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 6.8 g refined S-3-Aminomethyl-5-methylhexanoic acid was obtained. Yield ratio: 89.5% (optical purity %: 100%). Total yield ratio: 34%.

Example 2

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 36.7 g 4-methyl benzoyl-L-glutamic acid (Zhejiang Jiuzhou Pharmaceutical Co., Ltd., made by itself) and 200 ml water were added, then stirred and dissolved by heating, and maintained at that temperature for 10 minutes, cooled naturally to precipitate solids, then stirred at 10° C. for 20 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6.7 g 4-methyl benzoyl-L-glutamic acid and 150 ml water were added, then stirred and dissolved by heating, and maintained at that temperature for 10 minutes, cooled naturally to precipitate solids, then stirred at 10° C. for 20 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product and 100 ml water were added, then stirred and dissolved by heating, and maintained at that temperature for 10 minutes, cooled naturally to precipitate solids, then stirred at 10° C. for 2 hours, and filtered, the solids obtained were rinsed with the mother solution first and then a small amount of water, and pumped dry, thus 9.2 g refined resolution salt product was obtained. Yield ratio: 17.2%.

4. Hydrolysis

In a clean 250 ml 4-mouth flask, 9.2 g refined resolution salt product and 42 ml water were added, then stirred and 3.7 ml refined hydrochloric acid was added, after the product was dissolved, the solution was maintained at that temperature for 30 minutes, the resolution agent was extracted with (30+15+15) ml ethyl acetate, then the pH was adjusted to about 7 by adding about 10 ml 20% sodium hydroxide solution, the solution then was distilled under reduced pressure at 70~80° C. to about 15 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 3 g crude hydrolyte was obtained. Yield ratio: 87%.

5. Refinement

In a clean 100 ml 4-mouth flask, 3 g crude hydrolyte, 15 ml water and 15 ml isopropyl alcohol were added, then stirred and dissolved by heating, after dissolved completely, decolorized by adding 0.2 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 2.7 g refined S-3-Aminomethyl-5-methylhexanoic acid was obtained. Yield ratio: 90% (optical purity %: 100%). Total yield ratio: 13.5%.

Example 3

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 39.7 g benzene sulfonyl-L-glutamic acid (Zhejiang Jiuzhou Pharmaceutical Co., Ltd., made by itself) and 200 ml water were added, then stirred and dissolved by heating, and maintained at that temperature for 60 minutes, cooled naturally to precipitate solids, then stirred at 20~30° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 7.2 g benzene sulfonyl-L-glutamic acid and 150 ml water were added, then stirred and dissolved by heating, and maintained at that temperature for 60 minutes, cooled naturally to precipitate solids, then stirred at 20~30° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product and 100 ml water were added, then stirred and dissolved by heating, and maintained at that temperature for 60 minutes, cooled naturally to precipitate solids, then stirred at 20~30° C. for 2 hours, and filtered, the solids obtained were rinsed with the mother solution first and then a small amount of water, and pumped dry, thus 16.9 g refined resolution salt product was obtained. Yield ratio: 30.1%.

4. Hydrolysis

In a clean 250 ml 4-mouth flask, 16.9 g refined resolution salt product and 78 ml water were added, then stirred and 6.4 ml refined hydrochloric acid was added, after the product was dissolved, the solution was maintained at that temperature for 30 minutes, the resolution agent was extracted with (50+25+25) ml ethyl acetate, then the pH was adjusted to about 7 by adding about 17.8 ml 20% sodium hydroxide solution, the solution then was distilled under reduced pressure at 70~80° C. to about 30 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 5.4 g crude hydrolyte was obtained. Yield ratio: 89.6%.

5. Refinement

In a clean 100 ml 4-mouth flask, 5.4 g crude hydrolyte, 27 ml water and 27 ml isopropyl alcohol were added, then stirred and dissolved by heating, after dissolved completely, decolorized by adding 0.3 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 4.8 g refined S-3-Aminomethyl-5-methylhexanoic acid was obtained. Yield ratio: 889% (optical purity %: 100%). Total yield ratio: 24%.

Example 4

1. First Resolution

In a clean 250 ml 4-mouth flask, 20 g refined racemic 3-aminomethyl-5-methylhexanoic acid (Zhejiang Siuzhou Pharmaceutical Co., Ltd., HPLC≥98%), 41.6 g 4-methyl benzene sulfonyl-L-glutamic acid (Zhejiang Jiuzhou Pharmaceutical Co., Ltd., made by itself) and 200 ml water were added, then stirred and dissolved by heating, and maintained at that temperature for 15 minutes, cooled naturally to precipitate solids, then stirred at 80° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 7.6 g 4-methyl benzene sulfonyl-L-glutamic acid and 150 ml water were added, then stirred and dissolved by heating, and maintained at that temperature for 15 minutes, cooled naturally to precipitate solids, then stirred at 80° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product and 100 ml water were added, then stirred and dissolved by heating, and maintained at that temperature for 15 minutes, cooled naturally to precipitate solids, then stirred at 80° C. for 2 hours, and filtered, the solids obtained were rinsed with the mother solution first and then a small amount of water, and pumped dry, thus 14.5 g refined resolution salt product was obtained. Yield ratio: 25.1%.

4. Hydrolysis

In a clean 250 ml 4-mouth flask, 14.5 g refined resolution salt product and 67 ml water were added, then stirred and 5.3 ml refined hydrochloric acid was added, after the product was dissolved, the solution was maintained at that temperature for 30 minutes, the resolution agent was extracted with (40+20+20) ml ethyl acetate, then the pH was adjusted to about 7 by adding about 14.8 ml 20% sodium hydroxide solution, the solution then was distilled under reduced pressure at 70~80° C. to about 30 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 4.5 g crude hydrolyte was obtained. Yield ratio: 89.8%.

5. Refinement

In a clean 100 ml 4-mouth flask, 4.5 g crude hydrolyte, 22.5 ml water and 22.5 ml isopropyl alcohol were added, then stirred and dissolved by heating, after dissolved completely, decolorized by adding 0.2 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 4 g refined S-3-Aminomethyl-5-methylhexanoic acid was obtained. Yield ratio: 88.9% (optical purity %: 100%). Total yield ratio: 20%.

Example 5

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 34.5 g benzoyl-L-glutamic acid (Zhejiang Jiuzhou Pharmaceutical Co., Ltd., made by itself), 160 ml water and 40 ml methanol were added, then stirred and dissolved by heating, and maintained at that temperature for 15 minutes, cooled naturally to precipitate solids, then stirred at 20~30° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6 g benzoyl-L-glutamic acid, 120 ml water and 30 ml methanol were added, then stirred and dissolved by heating, and maintained at that temperature for 15 minutes, cooled naturally to precipitate solids, then stirred at 20~30° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product, 80 ml water and 20 ml methanol were added, then stirred and dissolved by heating, and maintained at that temperature for 15 minutes, cooled naturally to precipitate solids, then stirred at 20~30° C. for 2 hours, and filtered, the solids obtained were rinsed with the mother solution first and then a small amount of water, and pumped dry, thus 18 g refined resolution salt product was obtained. Yield ratio: 34.9%.

4. Hydrolysis

In a clean 250 ml 4-mouth flask, 18 g refined resolution salt product and 82.5 ml water were added, then stirred and 7.4 ml refined hydrochloric acid was added, after the product was dissolved, the solution was maintained at that temperature for 30 minutes, the resolution agent was extracted with (40+20+20) ml ethyl acetate, then the pH was adjusted to about 7 by adding about 20 ml 20% sodium hydroxide solution, the solution then was distilled under reduced pressure at 70~80° C. to about 35 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 6.2 g crude hydrolyte was obtained. Yield ratio: 88.8%.

5. Refinement

In a clean 250 ml 4-mouth flask, 6.2 g crude hydrolyte, 31 ml water and 31 ml isopropyl alcohol were added, then stirred and dissolved by heating, after dissolved completely, decolorized by adding 0.4 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 5.6 g refined S-3-Aminomethyl-5-methylhexanoic acid was obtained. Yield ratio: 90.3% (optical purity %: 100%). Total yield ratio: 28%.

Example 6

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 15.8 g benzoyl-L-glutamic acid (Zhejiang Jiuzhou Pharmaceutical Co., Ltd., made by itself) and 200 ml water were added, then stirred and dissolved by heating, and maintained at that temperature for 30 minutes, cooled naturally to precipitate solids, then stirred at 20~30° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6 g benzoyl-L-glutamic acid and 150 ml water were added, then stirred and dissolved by heating, and maintained at that temperature for 30 minutes, cooled naturally to precipitate solids, then stirred at 20~30° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product and 100 ml water were added, then stirred and dissolved by heating, and maintained at that temperature for 30 minutes, cooled naturally to precipitate solids, then stirred at 20~30° C. for 2 hours, and filtered, the solids obtained were rinsed with the mother solution first and then a small amount of water, and pumped dry, thus 10.5 g refined resolution salt product was obtained. Yield ratio: 20.4%.

4. Hydrolysis

In a clean 250 ml 4-mouth flask, 10.5 g refined resolution salt product and 50 ml water were added, then stirred and 4.3 ml refined hydrochloric acid was added, after the product was dissolved, the solution was maintained at that temperature for 30 minutes, the resolution agent was extracted with (25+10+10) ml ethyl acetate, then the pH was adjusted to about 7 by adding about 12 ml 20% sodium hydroxide solution, the solution then was distilled under reduced pressure at 70~80° C. to about 20 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 3.7 g crude hydrolyte was obtained. Yield ratio: 90.9%.

5. Refinement

In a clean 250 ml 4-mouth flask, 3.7 g crude hydrolyte, 18.5 ml water and 18.5 ml isopropyl alcohol were added, then stirred and dissolved by heating, after dissolved completely, decolorized by adding 0.2 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 3.3 g refined S-3-Aminomethyl-5-methylhexanoic acid was obtained. Yield ratio: 89.2% (optical purity %: 100%). Total yield ratio: 16.5%.

Example 7

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 47.3 g benzoyl-L-glutamic acid (Zhejiang Jiuzhou Pharmaceutical Co., Ltd., made by itself), 180 ml water and 18 ml isopropyl alcohol were added, then stirred and dissolved by heating, and maintained at that temperature for 15 minutes, cooled naturally to precipitate solids, then stirred at 30~40° C. for 4 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6 g benzoyl-L-glutamic acid, 150 ml water and 15 ml ethanol were added, then stirred and dissolved by heating, and maintained at that temperature for 15 minutes, cooled naturally to precipitate solids, then stirred at 30~40° C. for 4 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product, 100 ml water and 10 ml ethanol were added, then stirred and dissolved by heating, and maintained at that temperature for 15 minutes, cooled naturally to precipitate solids, then stirred at 30~40° C. for 2 hours, and filtered, the solids obtained were rinsed with the mother solution first and then a small amount of water, and pumped dry, thus 19.6 g refined resolution salt product was obtained. Yield ratio: 38%.

4. Hydrolysis

In a clean 250 ml 4-mouth flask, 19.6 g refined resolution salt product and 90 ml water were added, then stirred and 8.1 ml refined hydrochloric acid was added, after the product was dissolved, the solution was maintained at that temperature for 30 minutes, the resolution agent was extracted with (45+23+23) ml ethyl acetate, then the pH was adjusted to about 7 by adding about 22.5 ml 20% sodium hydroxide solution, the solution then was distilled under reduced pressure at 70~80° C. to about 35 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 6.8 g crude hydrolyte was obtained. Yield ratio: 89.5%.

5. Refinement

In a clean 250 ml 4-mouth flask, 6.8 g crude hydrolyte, 34 ml water and 34 ml isopropyl alcohol were added, then stirred and dissolved by heating, after dissolved completely, decolorized by adding 0.4 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 6.1 g refined S-3-Aminomethyl-5-methylhexanoic acid was obtained. Yield ratio: 89.7% (optical purity %: 100%). Total yield ratio: 30.5%.

Example 8

1. First Resolution

In a clean 250 ml 4-mouth flask, 20 g refined racemic 3-aminomethyl-5-methylhexanoic acid (Zhejiang Jiuzhou Pharmaceutical Co., Ltd., HPLC≥98%), 34.5 g benzoyl-L-glutamic acid (Zhejiang Jiuzhou Pharmaceutical Co., Ltd., made by itself), 135 ml water and 65 ml isopropyl alcohol were added, then stirred and dissolved by heating, and maintained at that temperature for 15 minutes, cooled naturally to precipitate solids, then stirred at 20~30° C. for 1 hours, and filtered, the solids obtained were rinsed with the mother solution first and then a small amount of water, and pumped dry, thus a first resolution product was obtained (the wet product is pumped dry as much as possible, and used directly in the next step of the second resolution).

2. Second Resolution

In a clean 250 ml 4-mouth flask, the above-mentioned first resolution product, 6 g benzoyl-L-glutamic acid, 100 ml water and 50 ml isopropyl alcohol were added, then stirred and dissolved by heating, and maintained at that temperature for 15 minutes, cooled naturally to precipitate solids, then stirred at 20~30° C. for 1 hours, and filtered, the solids obtained were rinsed with the mother solution first and then a small amount of water, and pumped dry, thus a second resolution product was obtained (the wet product is pumped dry as much as possible, and used directly in the next step of the refinement), thus a resolution salt product is obtained.

3. Refinement of the Resolution Salt Product

In a clean 250 ml 4-mouth flask, the above-mentioned resolution salt product, 65 ml water and 35 ml isopropyl alcohol were added, then stirred and dissolved by heating, and maintained at that temperature for 15 minutes, cooled naturally to precipitate solids, then stirred at 20~30° C. for 1 hours, and filtered, the solids obtained were rinsed with the mother solution first and then a small amount of water, and pumped dry, thus 18.6 g refined resolution salt product was obtained. Yield ratio: 36.1%.

4. Hydrolysis

In a clean 250 ml 4-mouth flask, 18.6 g refined resolution salt product, 55 ml water and 30 ml isopropyl alcohol were added, then stirred and 7.7 ml refined hydrochloric acid was added, after the product was dissolved, the solution was maintained at that temperature for 30 minutes, the resolution agent was extracted with (40+20+20) ml ethyl acetate, then the pH was adjusted to about 7 by adding about 21 ml 20% sodium hydroxide solution, the solution then was distilled under reduced pressure at 70~80° C. to about 35 ml, solids would be precipitated during the distillation process, then the solution was cooled with ice water, maintained at 0~5° C. for 1 hour, and filtered, the solids obtained were rinsed with the mother solution first and then a small amount of water, and pumped dry, thus 6.5 g crude hydrolyte was obtained. Yield ratio: 90.1%.

5. Refinement

In a clean 250 ml 4-mouth flask, 6.5 g crude hydrolyte, 32.5 ml water and 32.5 ml isopropyl alcohol were added, then stirred and dissolved by heating, after dissolved completely, decolorized by adding 0.4 activated carbon for half an hour, filtered when the solution was hot, the filtrate was heated again to dissolve the solids precipitated during the previous process, when the solids were dissolved completely, the solution was stirred slowly and cooled to precipitate the solids, then maintained at that temperature for 1 hour, cooled with ice water to 0~5° C. and maintained at that temperature for 1 hour, and filtered, the solids obtained were rinsed with the mother solution first and then a small amount of iced 50% (v/v) isopropyl alcohol aqueous solution and pumped dry, thus a wet product was obtained, and dried in 50~60° C. vacuum oven, then 5.8 g refined S-3-Aminomethyl-5-methylhexanoic acid was obtained. Yield ratio: 89.2% (optical purity %: 100%). Total yield ratio: 29%.

In summary, the present invention adopts benzoyl-L-glutamic acid, 4-methyl benzoyl-L-glutamic acid, benzene sulfonyl-L-glutamic acid or 4-methyl benzene sulfonyl-L-glutamic acid as a resolution agent to resolve racemic 3-aminomethyl-5-methylhexanoic acid to obtain the resolution salt product, the resolution salt product is hydrolyzed by an acid, the resolution agent is extracted, the pH is adjusted to be alkaline, the product S-3-(Aminomethyl)-5-methylhexanoic acid, i.e. the pregabalin, is then precipitated by distillation at high temperature under reduced pressure, therefore the present invention has the characteristics of polluting the environment slightly, high efficiency and stability, simpleness and practicality, producing product with high purity and a low production cost, and is suitable for large-scale production.

It should be noted that, all the documents mentioned in the present invention are cited as references in the present application, just as each document is cited individually as a references. In addition, it should also be understood that the content described above is the embodiments of the present invention and the technical principles used in the present invention, after reading the above content of the present invention, the technicians skilled in the art can make various modifications or changes to the present invention without departure from the spirit and scope of the present invention, these equivalent forms also fall within the scope of the present invention.

The invention claimed is:
1. A process for resolving S-3-(Aminomethyl)-5-methylhexanoic acid, comprising the following steps:
 a. Resolving racemic 3-aminomethyl-5-methylhexanoic acid as a raw material in a polar solvent by using benzoyl-L-glutamic acid, or 4-methyl-benzoyl-L-glutamic acid, or benzene sulfonyl-L-glutamic acid, or 4-methyl benzene sulfonyl-L-glutamic acid as a resolution agent, so as to obtain a resolution salt product;
 b. Hydrolyzing the resolution salt product by adding an acid, separating the resolution agent by extraction, adjusting pH to be neutral, then precipitating the product S-3-(Aminomethyl)-5-methylhexanoic acid by distillation.

2. The process for resolving S-3-(Aminomethyl)-5-methylhexanoic acid according to claim 1, wherein the resolution agent is benzoyl-L-glutamic acid or benzene sulfonyl-L-glutamic acid, the polar solvent is an aqueous solution or an alcohol aqueous solution; the resolving includes heating to dissolve the resolution agent and the raw material in the polar solvent, and maintaining that temperature for a period of time, then cooling, stirring and filtering the polar solvent to crystallize solids, washing and pumping the solids dry to obtain a first resolution product; the acid is hydrochloric acid, the separating the resolution agent by extraction adopts ethyl acetate, the pH is 7 and the temperature of the distillation is 70° C.~80° C.

3. The process for resolving S-3-(Aminomethyl)-5-methylhexanoic acid according to claim 2, wherein the resolution agent is benzoyl-L-glutamic acid; the solvent is water; the mole ratio of the resolution agent to the raw material is 0.5~1.5:1, the period of time is 10 minutes~60 minutes, the temperature of stirring is 10° C.~80° C., and the time of stirring is 1 hour~20 hours.

4. The process for resolving S-3-(Aminomethyl)-5-methylhexanoic acid according to claim 3, wherein the mole ratio of the resolution agent to the raw material is 1.1:1, the period of time is 15 minutes, the temperature of stirring is 20° C.~30° C., and the time of stirring is 4 hours.

5. The process for resolving S-3-(Aminomethyl)-5-methylhexanoic acid according to claim 2, wherein the alcohol aqueous solution is a methanol aqueous solution, an ethanol aqueous solution or an isopropyl alcohol aqueous solution, and the volume ratio of water to alcohol in the alcohol aqueous solution is 10:1~10:5.

6. The process for resolving S-3-(Aminomethyl)-5-methylhexanoic acid according to claim 2, wherein the resolving further includes making a second resolution to the first resolution product.

7. The process for resolving S-3-(Aminomethyl)-5-methylhexanoic acid according to claim 6, wherein the second resolution includes heating to dissolve the resolution agent and the first resolution product in the polar solvent, and maintaining that temperature for a period of time, then cooling, stirring and filtering the polar solvent to crystallize solids, washing and pumping the solids dry to obtain a second resolution product.

8. The process for resolving S-3-(Aminomethyl)-5-methylhexanoic acid according to claim 7, wherein the resolution agent of the second resolution is same to that of the first resolution, and the molar ratio of the resolution agent of the second resolution to the first resolution product is 0~1:1.

9. The process for resolving S-3-(Aminomethyl)-5-methylhexanoic acid according to claim 8, wherein the molar ratio of the resolution agent of the second resolution to the first resolution product is 0.4:1.

10. The process for resolving S-3-(Aminomethyl)-5-methylhexanoic acid according to claim 1, wherein after the step a and before the step b, the process further comprises the step:
  a1. Refining the resolution salt product by crystallization.

11. The process for resolving S-3-(Aminomethyl)-5-methylhexanoic acid according to claim 1, wherein after the step b, the process further comprises the step:
  b1. Heating to dissolve the product S-3-(Aminomethyl)-5-methylhexanoic acid in a 50% (v/v) isopropyl alcohol aqueous solution, decolorizing the solution with activated carbon and filtering the solution, then refining the product by crystallization.

* * * * *